United States Patent [19]
Clapp et al.

[11] Patent Number: 5,626,145
[45] Date of Patent: May 6, 1997

[54] METHOD AND APPARATUS FOR EXTRACTION OF LOW-FREQUENCY ARTIFACTS FROM BRAIN WAVES FOR ALERTNESS DETECTION

[75] Inventors: Ned E. Clapp; Lee M. Hively, both of Knoxville, Tenn.

[73] Assignee: Lockheed Martin Energy Systems, Inc., Oak Ridge, Tenn.

[21] Appl. No.: 619,031

[22] Filed: Mar. 20, 1996

[51] Int. Cl.⁶ .................................................. A61B 5/04
[52] U.S. Cl. ............................................ 128/731; 128/732
[58] Field of Search .............................. 128/731, 732

[56] References Cited

U.S. PATENT DOCUMENTS

| 5,311,876 | 5/1994 | Olsen et al. | 128/731 |
| 5,349,962 | 9/1994 | Lockard et al. | 128/732 |
| 5,392,788 | 2/1995 | Hudspeth | 128/731 |

OTHER PUBLICATIONS

Frank H. Duffy, Vasudeva G. Iyer, and Walter W. Surwillo "Clinical electroencephalography and topographic brain mapping," Springer–Verlag New York, Inc. 1989.

Stern, John A. Donna Boyer, David Schrueder "Blink Rate: A Possible Measure of Fatigue" Human Factors and Ergonomics Jun. 1994.

*Primary Examiner*—Lee S. Cohen
*Assistant Examiner*—Stephen D. Huang
*Attorney, Agent, or Firm*—J. Kenneth Davis

[57] ABSTRACT

Methods and apparatus automatically detect alertness in humans by monitoring and analyzing brain wave signals. Steps include: acquiring the brain wave (EEG or MEG) data from the subject, digitizing the data, separating artifact data from raw data, and comparing trends in f-data to alertness indicators, providing notification of inadequate alertness.

14 Claims, 3 Drawing Sheets

METHOD AND APPARATUS FOR EXTRACTION OF LOW-FREQUENCY ARTIFACTS FROM BRAIN WAVES FOR ALERTNESS DETECTION

The United States Government has rights in this invention pursuant to contract no. DEAC05-84OR21400 between the United States Department of Energy and Lockheed Martin Energy Systems, Inc.

FIELD OF THE INVENTION

The present invention relates to the use of human electroencephalogram (EEG) data and magnetoencephalogram (MEG) data for detecting alertness, and more particularly to the use of a zero-phase filter for separating artifact data from raw data to enable the artifact data to be examined for indicators of fatigue and/or drowsiness.

CROSS-REFERENCE TO RELATED APPLICATIONS

This invention is related to U.S. Ser. No. 08/619,024 Epileptic Seizure Detection by Non-linear Methods by Lee M. Hively, Ned E. Clapp, C. Stuart Daw, and William F. Lawkins and to U.S. Ser. No. 08/619,030 Epileptic Seizure Prediction by Non-linear Methods by Lee M. Hively, Ned E. Clapp, C. Stuart Daw, and William F. Lawkins, both of which are filed on even date herewith, and both of which are assigned to the same entity.

BACKGROUND OF THE INVENTION

It has long been accepted that in humans, blinking of the eyes serves to cleanse and lubricate the corneal surface, and that the rate of blinking and other measures of blinking could be attributed to environmental conditions (such as humidity and particulates in the air). It has also been postulated by investigators that blinking is strongly influenced by other factors such as fatigue and drowsiness, and may be monitored to provide some indication of alertness, which is used herein to mean the absence of fatigue and drowsiness.

The ability to measure alertness, or to detect the absence of alertness or presence of fatigue or drowsiness is desired. Many work assignments require a high level of alertness, often in environments not conducive to maintaining alertness. Examples of these are: nuclear reactor operators, aircraft pilots and other operators of complex equipment, air traffic controllers and others whose work environments provide little visual stimulus of a non-monotonous nature. Often consequences of lapses in alertness in these conditions can be grave, involving a high degree of hazard to life and property. It is this connection that has led the inventors to develop this method and apparatus for detection of alertness.

OBJECTS OF THE INVENTION

Accordingly, it is an object of the present invention to provide new and improved methods and apparatus for extraction of low-frequency artifacts from brain waves to permit use of the artifact data for detecting alertness in subjects.

It is a second object to provide a new and improved zero-phase filter for use in separating artifact brain wave data from raw brain wave data to permit using the artifact data to detect alertness in subjects.

Further and other objects of the present invention will become apparent from the description contained herein.

SUMMARY OF THE INVENTION

In accordance with one aspect of the present invention, the foregoing objects are achieved by a method for automatically extracting low-frequency artifacts from brain waves which comprises the steps of: providing at least one channel of raw brain wave data, called e-data, selected from the group consisting of electroencephalogram data and magnetoencephalogram data; and separating artifact data, called f-data, from the e-data while preventing phase distortions in the data, by passing the e-data through a zero-phase quadratic filter which provides an output of f-data, whereby the f-data may be further analyzed to detect alertness.

In accordance with a second aspect of the present invention, the foregoing and other objects are achieved by apparatus for automatically detecting alertness in a subject which comprises: data provision means for providing at least one channel of the subject's raw brain wave data, called e-data, selected from the group consisting of electroencephalogram data and magnetoencephalogram data; and separation means for separating artifact data, called f-data, from the e-data while preventing phase distortions in the data, said separation means comprising a zero-phase quadratic filter providing an output of f-data, said separation means communicably connected to said data provision means, whereby the f-data may be further analyzed to detect alertness.

In accordance with a third aspect of the present invention, the foregoing and other objects are achieved by a zero-phase filter for separating artifact brain wave data from raw brain wave data selected from the group consisting of electroencephalogram data and magnetoencephalogram data comprises a zero-phase quadratic filter wherein the data is fit to a quadratic equation that takes the form $F_i = F(t_i) = a_1(t_i - t_c)^2 + a_2(t_i - t_c) + a_3 = a_1 T_i^2 + a_2 T_i + a_3$; wherein $t_c = c\Delta t$ is the time at the central point, and $T_i = t_i - t_c$; this approximation is fitted to the data, by minimizing the sum of squares of the differences between the quadratic equation, F(t), and the raw electroencephalogram data, e(t), corresponding to the minimum in the function $$L = \sum_{i=c-n}^{c+n} [F(t_i) - e(t_i)]^2 = \sum_{i=-n}^{n} [(a_1 T_i^2 + a_2 T_i + a_3) - e_{i+c}]^2;$$

the minimum in L is found from the condition $\partial L/\partial a_k = 0$, for $k = \{1, 2, 3\}$, forming three simultaneous linear equations in three unknowns; the window-averaged artifact ($F_c$) is given by the fitted value of the central point, $F_c = F(0) = a_3$; the sums over odd powers of $T_i$ are zero and symmetric sums over even powers of $T_i$ (over i from $-n$ to $+n$) can be converted to sums from 1 to n with $T_i = i\Delta t$, yielding a window-averaged solution for the artifact signal $$F_c = \frac{3(3n^2 + 3n - 1)(\Sigma_i e_{i+c}) - 15(\Sigma_i i^2 e_{i+c})}{(4n^2 + 4n - 3)(2n + 1)};$$

and the filter is embodied a programmed integrated circuit semiconductor chip.

Figure 1:
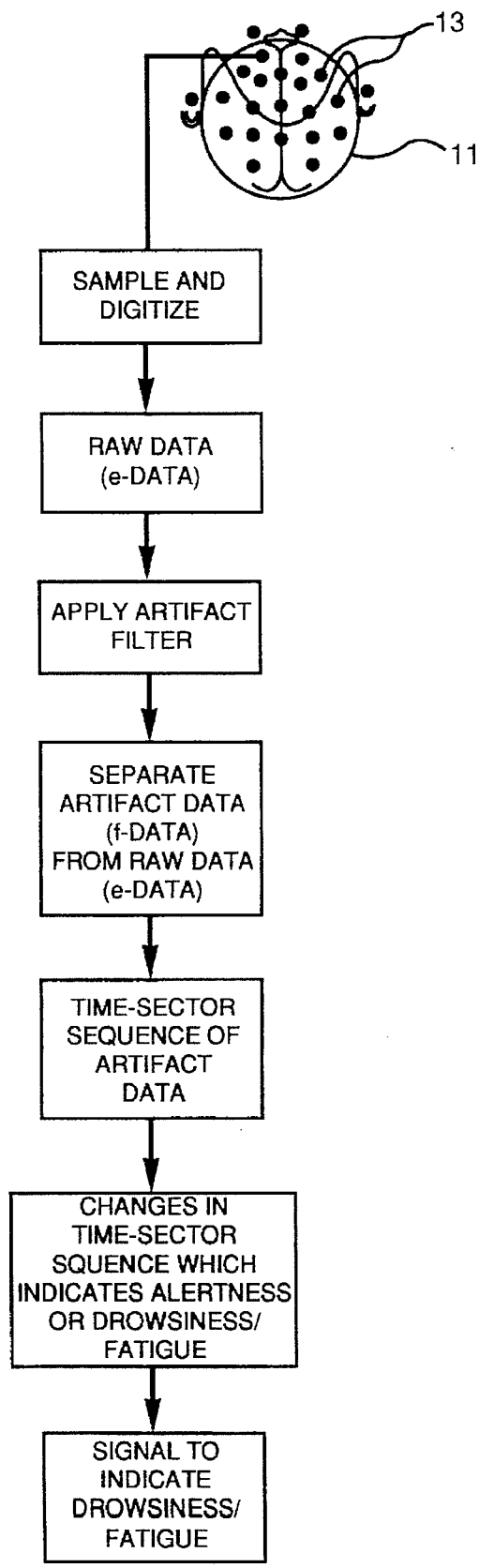
FIG. 1 is a block diagram showing how brain wave data is obtained from the subject, digitized, processed, and analyzed to detect alertness, drowsiness, or fatigue. 11 shows the patient's head, looking from above. 13 shows EEG electrode positions on the patient's scalp. 15 shows a measure of alertness, drowsiness, or fatigue.
Figure 2:
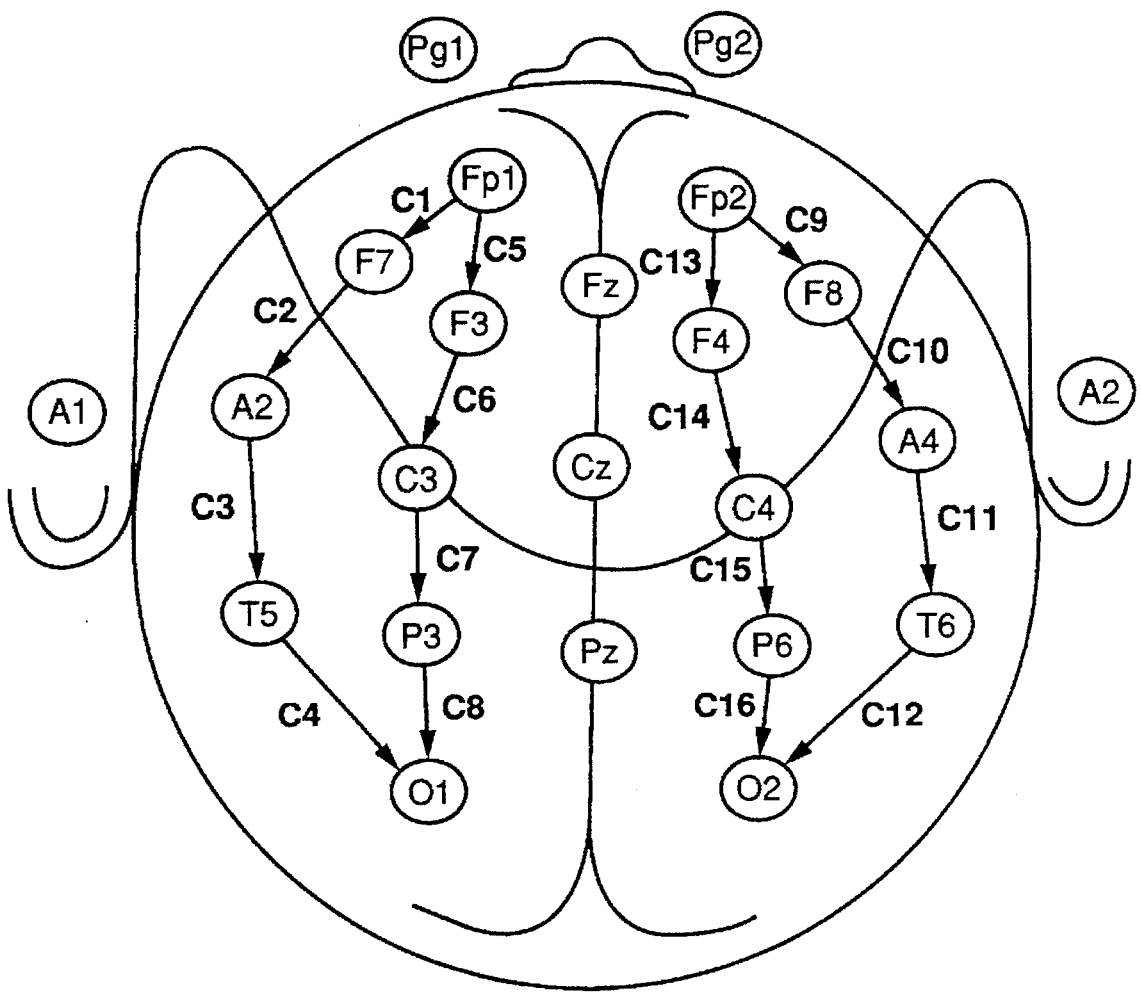
FIG. 2 shows standard EEG electrode positions on a patient's scalp for the bipolar montage, looking from above. C13 labels the position where the channel 13 data, which is used in this work originates.

For a better understanding of the present invention, together with other and further objects, advantages and capabilities thereof, reference is made to the following disclosure and appended claims in connection with the above-described drawings.

DETAILED DESCRIPTION OF THE INVENTION

This invention has been developed as an adjunct to the development of methods and apparatus for detection and prediction of epileptic seizures by non-linear methods. In that work, it was necessary to develop methods and apparatus for separating certain brain-wave (EEG or MEG) data from other data in order to detect and/or predict seizures. The data that was separated was primarily "artifact" data, that is data resulting from eye blinks, chewing, and other movements not related to brain activity. The separation of these types of data had to be done without disturbing phase relationships within the data in order for the seizure detection and prediction methods to be effective.

In the work described herein, sixteen channels of EEG data were analyzed. The data were retrieved in analog form from VHS tapes and convened to digital form with 12-bit precision, giving an integer between −2048 and +2047. The digital sampling rate ($f_s$) was 512 Hz over a total sample time of 10–23 minutes, corresponding to a total dataset size of 9.8–22.5 megabytes in binary form.

It is acknowledged that to detect drowsiness or fatigue, or to detect alertness, as it occurs, the brain wave data used would not be recorded data, but would be currently-occurring data. This data would be taken from the patient to the apparatus directly using standard EEG or MEG methods, or other more convenient convenient means such as eyeglasses, a hat, headband, or the like that would comprise the means for picking up the signal from the subject. The eyeglasses, hat, headband, or the like would be communicably connected directly to the means for separating the artifact data from the raw data, or indirectly by transmitting the data to an apparatus remote from the patient by means such as telephone, radio, or other communications means well known to the skilled artisan.

Accordingly, a zero-phase quadratic filter was developed for use in separating the "clean" brain wave data from the artifact data. Now, in this invention a second use for the filter is found, and the artifact data is put to new use in a method and apparatus for alertness detection.

The method is accomplished by monitoring brain waves as recorded in standard digital electroencephalogram (EEG) data or magnetoencephalogram (MEG) data, separating from the raw data artifact data, including indications of eye blinks, twitches, movements of the head and jaw, etc., analyzing the artifact data for patterns of eye blinks that indicate fatigue or drowsiness, detecting indications of fatigue or drowsiness, and providing an indication of fatigue to the subject or other person or data system.

In the course of developing methods and apparatus for using raw EEG or MEG data, hereinafter called e-data, to detect and predict epileptic seizures, it was necessary for the inventors to separate artifact data from raw data in order to process the artifact-free data and detect or predict epileptic seizure. The artifact data is used in the present invention for alertness detection. In order to separate the artifact data from the raw data while preserving phase relationships and characteristics in both the artifact-free data and the artifact data, it was necessary to develop a zero-phase filter and method for using the filter.

John A. Stern, Donna Boyer, and David Schroeder, in *Human Factors*, 1994, 36(2), pp 285–297, indicates that researchers "have been less concerned with physical and environmental factors responsible for the act of blinking and more concerned with psychological or behavioral variables that may affect blink rate. One such factor is fatigue, a term difficult to define, especially if one prefaces it with the term mental. Physical fatigue is generally defined with respect to a reduction in capacity to perform physical work as a function of immediately preceding physical effort. Mental fatigue is inferred from decrements in performance on tasks requiting alertness and the manipulation and retrieval of information stored in memory." Stern et al. suggest that mental fatigue is physiologically measurable, and further single out the eye blink as a major reflector of mental fatigue processes.

Stern et al. also note that it is their "contention that the application of electrodes for the recording of variables of interest is acceptable in laboratory investigations but is, for a variety of reasons, not possible in real-world attempts at monitoring attentional processes."

Blink Rate: A Possible Measure of Fatigue, *Human Factors*, 1994, 36(2), pages 285–297 by John A. Stern, Donna Boyer, and David Schroeder is hereby incorporated by reference.

Because the raw EEG data used in this study was taken from only one channel of a standard sixteen-channel standard EEG data set, this invention demonstrates that Stern et al contend invalidly that "the application of electrodes for the recording of variables of interest is acceptable in laboratory investigations but is, for a variety of reasons, not possible in real-word attempts at monitoring attentional processes." Data can be easily taken by one or a few electrodes mounted in eyeglasses, hat, headband or other easily-worn or easily-attached device on the head, contacting the scalp. From the electrode or electrodes, data is transmitted to the apparatus which digitizes, filters, and analyzes the data and provides notification or alarm.

EEG and MEG brain wave data contains not only signals associated with brain activity, but also has artifacts (e.g., eye blinks, muscle twitches, chewing, etc.) that obscure the brain-wave signal. In developing methods and apparatus for epileptic seizure detection and prediction by non-linear methods, a novel zero-phase filter was developed to remove low-frequency artifacts, based on the following criterion. A zero-phase-shift filter was needed to prevent phase distortions when subtracting the filter output (the "artifact" signal) from the EEG signal to yield an undistorted artifact-filtered or artifact-free signal, because phase relationships are most important in the subsequent nonlinear analysis. Standard high-pass filter techniques do not meet this criterion. A computationally fast, simple, low-frequency signal follower was necessary to eventually apply the filter in real- or near-real time. Consequently, quadratic regression analysis was used, with the same number of data samples on either side of a central point. Other standard digital filtering methods (45) could not meet this requirement.

The zero-phase filter method, which could be embodied in an integrated-circuit chip, is as follows. For a specific EEG channel, the signal (e) at time (t) is sampled at regular intervals ($t_i=i\Delta t$) to yield a set of time serial data $e_i=e(t_i)$. We selected a filter-window length of 2n+1 points from the time series, where n is the number of points on either side of the central point ($e_c$) as indicated in the sequence below.

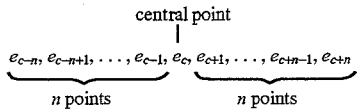

The data was fitted to a quadratic equation that takes the form: $F_i=F(t_i)=a_1 (t_i-t_c)^2+a_2 (t_i-t_c)+a_3=a_1 T_i^2+a_2 T_i+a_3$. Here, $t_c=c\Delta t$ is the time at the central point, and $T_i=t_i-t_c$. This approximation is fitted to the data, by minimizing the sum of squares of the differences between the quadratic equation, F(t), and the raw EEG data, e(t), corresponding to the minimum in the following function:

$$L = \sum_{i=c-n}^{c+n} [F(t_i) - e(t_i)]^2 = \sum_{i=-n}^{n} [(a_1 T_i^2 + a_2 T_i + a_3) - e_{i+c}]^2 \quad (1)$$

The minimum in L is found from the condition $\partial L/\partial a_k=0$, for k={1, 2, 3}, forming three simultaneous linear equations in three unknowns. The window-averaged artifact ($F_c$) is given by the fitted value of the central point, $F_c=F(0)=a_3$. Note that the sums over odd powers of $T_i$ are zero and that symmetric sums over even powers of $T_i$ (over i from −n to +n) can be converted to sums from 1 to n with $T_i=i\Delta t$, yielding a window-averaged solution for the artifact signal:

$$F_c = \frac{3(3n^2 + 3n - 1)(\Sigma_i e_{i+c}) - 15(\Sigma_i i^2 e_{i+c})}{(4n^2 + 4n - 3)(2n + 1)} \quad (2)$$

Here, $\Sigma_i$ indicates the sum over i from −n to +n. Sums over even powers of "i" were explicitly evaluated with standard formulae (36). The effort to evaluate $F_c$ can be reduced substantially by computing the sums initially from Eq. 2 (at c=n+1), and then using the following recursions thereafter:

$$\sum_{i=-n}^{n} e_{i+c+1} = e_{c+n+1} - e_{c-n} + \sum_{i=-n}^{n} e_{i+c} \quad (3)$$

$$\sum_{i=-n}^{n} i e_{i+c+1} = \quad (4)$$

$$ne_{c+n+1} + (n+1)e_{c-n} + \sum_{i=-n}^{n} i e_{i+c} - \sum_{i=-n}^{n} e_{i+c}$$

$$\sum_{i=-n}^{n} i^2 e_{i+c+1} = n^2 e_{c+n+1} - (n+1)^2 e_{c-n} +$$

$$\sum_{i=-n}^{n} i^2 e_{i+c} - 2 \sum_{i=-n}^{n} i e_{i+c} + \sum_{i=-n}^{n} e_{i+c} \quad (5)$$

The right-hand sides of Eqs. 3–5 only involve the sums previously computed. Application of Eqs. 2–5 to the N-point set of original time serial EEG data ($e_i$) yields an artifact dataset ($f_i$- or f-data) with (N−2n) points that contains the low frequency artifact signal.

Figure 3A:
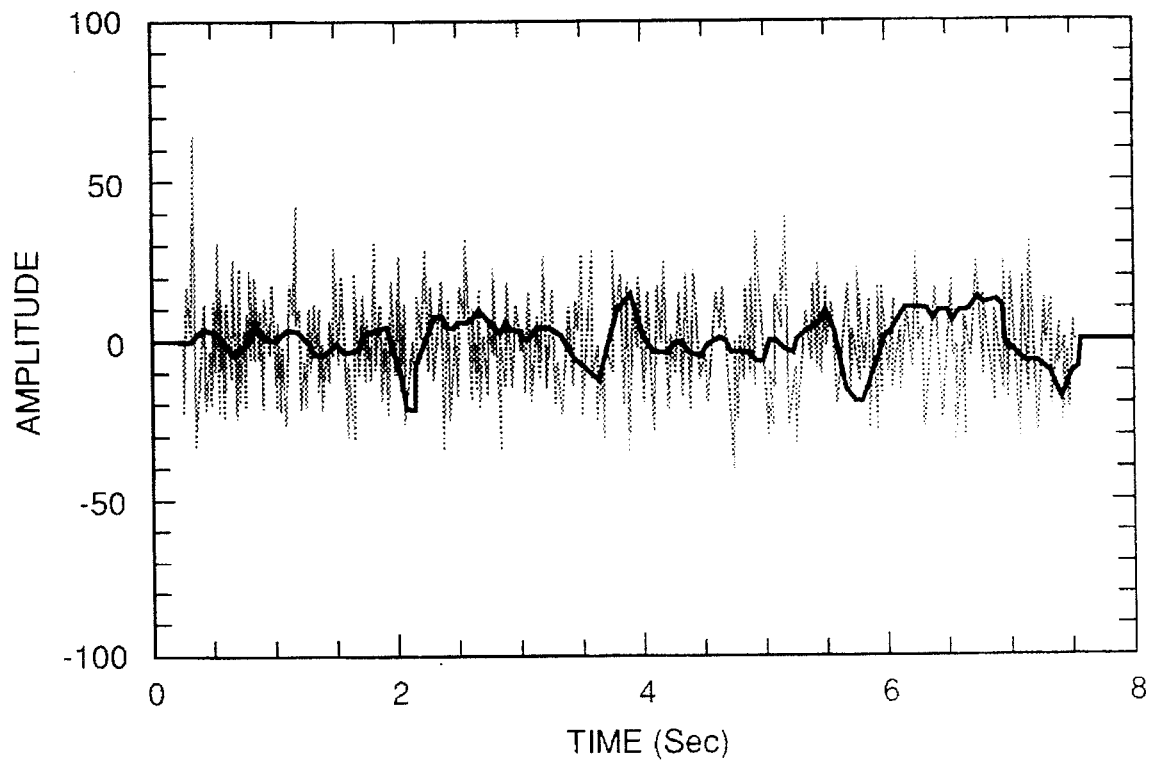
FIG. 3 shows sample plots of EEG data, and compares raw (e-data) with artifact-filtered (g-data).
Figure 3B:
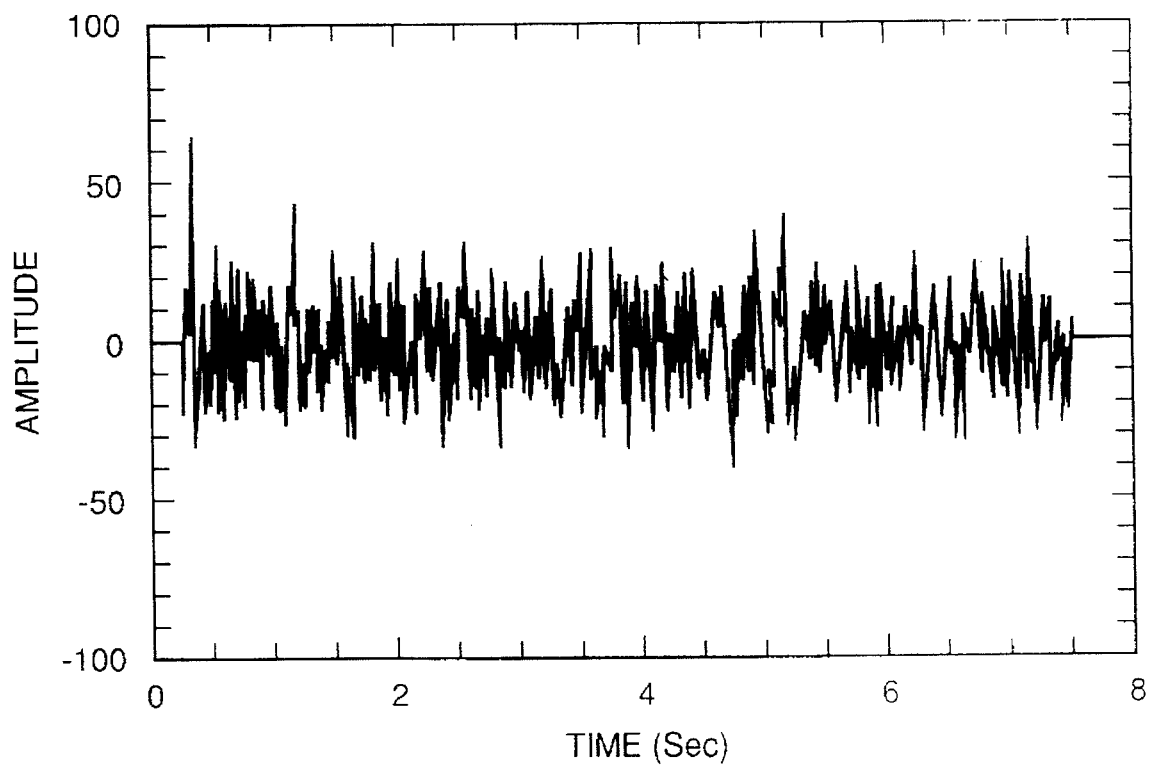

The filter-window length (n=128) corresponds to a frequency of 2.0 Hz [=512 Hz/(2n+1)]. FIG. 3a shows an example of the application of this method, with (raw) e-data in light gray and a superimposed (dark line) artifact signal (f-data), which clearly follows the low-frequency trends. FIG. 3b shows the residual signal (g-data) for this example, as having little low-frequency component while retaining the higher frequency information.

In one embodiment, eyelid movement, or eye blinks are detected and analyzed to monitor alertness and detect drowsiness or fatigue. Changes in eye blink such as frequency of blinks, and more especially changes in the period when the eye is closed may be interpreted as indicators of fatigue or drowsiness.

Eye-blink artifact can be recognized as a triangular waveform present in channel 5 and 13 using the bipolar montage. The triangular waveform for eye-blink has a duration of about 0.2 seconds. The eye-blink artifact normally occurs as multiple events where the time period between blinks is on the order of one second. The eye-blink artifact can be detected using a finite-impulse response (FIR) digital filter that has been timed to detect the eye-blink waveform. The peak output of the eye-blink FIR corresponds to the center of the eye-blink waveform.

In other embodiments, other artifacts such as yawns and other movements of the head, jaw, or eyes may be detected and used, instead of or in conjunction with, eye blink artifacts to indicate alertness or absence of alertness.

While there has been shown and described what are at present considered the preferred embodiments of the invention, it will be obvious to those skilled in the art that various changes and modifications can be made therein without departing from the scope of the inventions defined by the appended claims.

What is claimed is:

1. A method for automatically extracting low-frequency artifact data from brain wave data comprising the steps of:
    (a) utilizing a standard method selected from the group of methods consisting of electroencephalogram method and magnetoencephalogram method to provide at least one channel of raw brain wave data, called e-data, selected from the group consisting of electroencephalogram data and magnetoencephalogram data; and
    (b) separating artifact data, called f-data, from the e-data while preventing phase distortions in the data, by passing the e-data through a zero-phase filter means for providing an output of f-data, whereby the f-data may be further analyzed to detect alertness.

2. The method as described in claim 1 wherein said zero-phase filter means comprises an integrated circuit chip zero-phase filter.

3. The method described in claim 2 wherein recursions are used with the f-data from the zero-phase filter means described in claim 2 to yield artifact data.

4. Apparatus for automatically extracting low-frequency artifact data from brain wave data comprising:
    (a) data provision means selected from the group of means consisting of electroencephalogram means and magnetoencephalogram means for providing at least one channel of raw brain wave data, called e-data, selected from the group consisting of electroencephalogram data and magnetoencephalogram data; and
    (b) separation means for separating artifact data, called f-data, from the e-data while preventing phase distortions in the data, said separation means comprising a zero-phase filter means for providing an output of f-data, said separation means communicably connected to said data provision means, whereby the f-data may be further analyzed to detect alertness.

5. The apparatus as described in claim 4 wherein said zero-phase filter means comprises an integrated circuit chip zero-phase filter.

6. The apparatus described in claim 5 wherein recursions are used with the f-data from the zero-phase filter means described in claim 5 to yield artifact data.

7. A zero-phase filter for separating artifact brain wave data, called f-data, from raw brain wave data, called e-data, selected from the group consisting of electroencephalogram data and magnetoencephalogram data, said zero-phase filter comprising an integrated circuit chip zero-phase filter for separating artifact brain wave data from raw brain wave data while preventing phase distortions in the data.

8. The integrated circuit chip zero-phase filter described in claim 7 wherein recursions are used with the f-data from the zero-phase filter means described in claim 7 to yield artifact data.

9. A method for automatically detecting a subject's state of alertness from the subject's brain wave data comprising the steps of:

(A) utilizing a standard method selected from the group of methods consisting of electroencephalogram method and magnetoencephalogram method to provide at least one channel of raw brain wave data, called e-data, selected from the group consisting of electroencephalogram data and magnetoencephalogram data;

(B) separating artifact data, called f-data, from the e-data while preventing phase distortions in the data, by passing the e-data through a zero-phase filter means for providing an output of f-data;

(C) analyzing the f-data to detect indications of fatigue or drowsiness, thereby detecting a lack of alertness; and (D) providing an indication of the lack of alertness.

10. The method as described in claim 9 wherein said zero-phase filter means comprises an integrated circuit chip zero-phase filter.

11. The method described in claim 10 wherein recursions are used with the f-data from the zero-phase filter means described in claim 10 to yield artifact data.

12. Apparatus for automatically detecting a subject's state of alertness from the subject's brain wave data comprising:

(A) data provision means selected from the group of means consisting of electroencephalogram means and magnetoencelaphogram means for providing at least one channel of raw brain wave data, called e-data, selected from the group consisting of electroencephalogram data and magnetoencephalogram data;

(B) separation means for separating artifact data, called f-data, from the e-data while preventing phase distortions in the data, said separation means comprising a zero-phase filter means for providing an output of f-data, said separation means communicably connected to said data provision means;

(C) analysis means for analyzing the f-data to detect indications of fatigue or drowsiness, thereby detecting a lack of alertness, said analysis means communicably connected to said separation means; and (D) indication means for providing an indication of the lack of alertness, said indicator means communicably connected to said analysis means.

13. The apparatus as described in claim 12 wherein said zero-phase filter means comprises an integrated circuit chip zero-phase filter.

14. The apparatus described in claim 13 wherein recursions are used with the f-data from the zero-phase filter means described in claim 13 to yield artifact data.

* * * * *